United States Patent [19]

Martini

[11] 4,118,399

[45] Oct. 3, 1978

[54] PROCESS FOR PREPARING PERFLUORO-α-(3,6-DIMETHYL-1,4-DIOXANYL-2-OXY)-PROPIONIC ACID FLUORIDE

[75] Inventor: Thomas Martini, Bad Soden am Taunus, Fed. Rep. of Germany

[73] Assignee: Hoechst Aktiengesellschaft, Frankfurt am Main, Fed. Rep. of Germany

[21] Appl. No.: 798,311

[22] Filed: May 19, 1977

[30] Foreign Application Priority Data

May 22, 1976 [DE] Fed. Rep. of Germany ....... 2623090

[51] Int. Cl.² .......................................... C07D 319/12
[52] U.S. Cl. .............................. 260/340.2; 260/340.6
[58] Field of Search .......................... 260/340.2, 340.6

[56] References Cited

U.S. PATENT DOCUMENTS

| | | | |
|---|---|---|---|
| 3,404,162 | 10/1968 | Selman | 260/340.2 |
| 3,962,279 | 6/1976 | England | 260/340.2 |
| 4,033,984 | 7/1977 | Martini | 260/340.6 |
| 4,035,388 | 7/1977 | Martini | 260/340.6 |

FOREIGN PATENT DOCUMENTS 2,434,992  2/1976  Fed. Rep. of Germany.

Primary Examiner—Norma S. Milestone
Attorney, Agent, or Firm—Curtis, Morris & Safford

[57] ABSTRACT

By reacting an N-formylated secondary amine with hexafluoro epoxide in the presence of trisdimethyl amino difluorophosphorane or hexamethyl phosphoric acid triamide mixture can be obtained consisting of perfluoro-α-(3,6-dimethyl-1,4-dioxanyl-2-oxy)-propionic acid fluoride and perfluoro-2-oxo-3,6-dimethyl-1,4-dioxane.

2 Claims, No Drawings

PROCESS FOR PREPARING PERFLUORO-α-(3,6-DIMETHYL-1,4-DIOXANYL-2-OXY)-PROPIONIC ACID FLUORIDE

It is known from U.S. Pat. No. 3,450,716 that ketones and aldehydes react with hexafluoropropene epoxide (HFPO) at 100° to 300° C. This reaction produces also perfluoro pyruvic acid fluoride or the cyclic dimer thereof, the perfluoro-4-oxo-2,5 dimethyl-2-fluorocarbonyl-1,3-dioxolane (PODF). It has been found now that the preparation of PODF may be improved and may especially be carried out under normal pressure and at lower temperatures, when hexafluoropropene epoxide is reacted at a temperature from $-50°$ to $+20°$ C. with an N-formylated, secondary amine, when non-reacted hexafluoropropene epoxide is removed and when the perfluorinated dioxolane is isolated from the reaction products.

This process may be described by the following reaction scheme, if dimethyl formamide is used as N-formylated secondary amine:

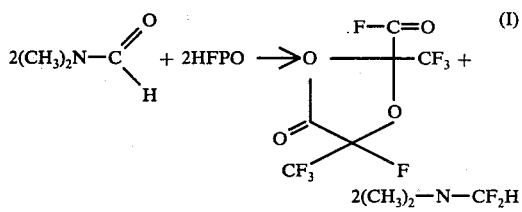

If this reaction is carried out in the presence of tris-dimethyl amino difluoro phosphorane or of hexamethyl phosphoric acid triamide (HMPT) which reacts under the reaction conditions with HFPO to trisdimethylamino difluorophosphorane and perfluoro-α-(3,6-dimethyl-1,4-dioxanyl-2-oxy)-propionic acid fluoride, and particularly with an excess of HFPO, the reaction procedes through the stage of PODF, while forming perfluoro-α-(3,6-dimethyl-1,4-dioxanyl-2-oxy)-propionic acid fluoride (II) and perfluoro-2-oxo-3,6-dimethyl-1,4-dioxane (III).

Subject of the present invention is therefore a process for preparing perfluoro-α-(3,6-dimethyl-1,4-dioxanyl-2-oxy)-propionic acid fluoride (II) and/or perfluoro-2-oxo-3,6-dimethyl-1,4-dioxane (III), which comprises reacting an N-formylated secondary amine with hexafluoropropene oxide in the presence of trisdimethylamino-difluorophosphorane (IV) at temperatures from $-40°$ to $+5°$ C., preferably from $-25°$ to $-10°$ C.

This reaction follows the reaction scheme stated below:

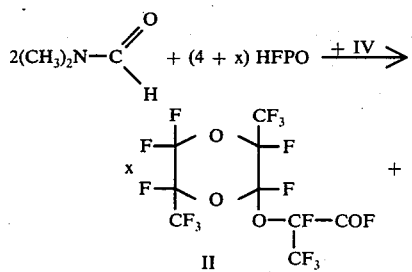

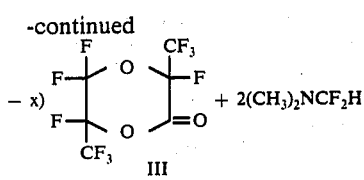

with $x = 0$ to 2.

Stoichiometry requires: for the formation of one mole of compound II at least 3 moles of HFPO/1 mole of N-formylated secondary amine. For the formation of 1 mole of compound III there are needed at least 2 moles of HFPO/1 mole of N-formylated secondary amine.

Both reaction products are important intermediate products. Compound II may be converted to the corresponding perfluorovinyl ether by decarboxylation, said ether representing an important copolymer for the preparation of paste - extrudable tetrafluoroethylene polymers.

Compound III may be converted to perfluoro-(2-methylene-4-methyl-1,3-dioxolane) of formula

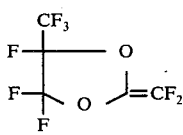

according to U.S. Pat. Nos. 3,450,716 and 3,308,107, which compound is used for the preparation of homopolymers and copolymers, especially for copolymerization with tetrafluoroethylene. Moreover, compound III may be transformed into the compound II with further quantities of HFPO under the catalytic influence of tris-dimethylamino-difluorophosphorane.

The practical realization of the process according to the invention yields, in general, mixtures of the compounds II and III. Even in the presence of excess quantities of HFPO (X>2) still portions of product III and non-reacted HFPO are formed, the quantities of which depend also upon the reaction temperature and the reaction time. Even if HFPO is deficient (less than 4 moles of HFPO per 2 moles of N-formylated secondary amine), there are still obtained mixtures of the compounds II and III, preferably however the compound III in addition to non-reacted N-formylated secondary amine. Perfluoro pyruvic acid fluoride or PODF (compound I) are found, in the presence of trisdimethylaminodifluorophosphorane (IV), in very small amounts.

These data prove that the ratio of N-formylated secondary amine to HFPO is not critical at all for the feasibility of the process according to the invention, though this detail greatly influences the quantity ratios of the final products II and III. If the desired product is mainly compound II, it is useful to stick to a ratio of N-formylated secondary amine to HFPO from 2:5 to 2:7 or more, e.g. 2:10. On the other hand, if the main interest focuses on compound III, this ratio is usefully kept within the range of 2:3 to 2:4 or less, e.g. 2:0.5.

The quantity of tris(dimethylamino)difluorophosphorane (IV) to be added as catalyst is not critical. A quantity of from 0.01 to 0.02 mole/mole of N-formylated secondary amine still yields good results. There is no upper limit to the quantity of catalyst. However, one of the advantages of the process according to the invention resides in the fact that even minor quantities of compound IV which has to be made from carcinogenic HMPT, are sufficient. Therefore, the best choice for the amount of compound IV is from 0.01 and 0.5 mole, preferably from 0.02 and 0.2 mole per mole of N-formylated secondary amine. If HMPT is used instead of compound IV, the quantity of HFPO has to be increased for the amount required for the conversion to compound III.

The process according to the invention may be carried out in the presence of inert solvents. Aprotic polar solvents, especially ethers such as diethylene glycol dimethyl ether or tetraethylene glycol dimethyl ether are particularly well suited to that purpose. There may also be used nitriles such as acetonitrile or propionitrile. The quantity of solvent is not critical, preferably are used from 0.15 to 1.0 part by volume per part by volume of N-formylated secondary amine. The use of an aprotic-polar solvent not only accelerates the reaction speed, but has the additional advantage that the process leads to a biphased mixture, one phase of which essentially contains the solvent and the difluorinated tertiary amine, while the other phase essentially includes the reaction products II and III.

HFPO may be used as such or also in admixture with hexafluoropropene (HFP). Preference is given to the use of a technological mixture with HFP consisting of about 65 weight % of HFPO and 35 weight % of HFP.

Though reaction temperatures of higher then +20° C., e.g. up to 50° C. are possible, they easily cause decomposition of the products and reduction of the yield. On the other hand, reaction temperatures below −50° C. bring about a substantial reduction in the rate of the reaction.

The structure of the N-formylated secondary amine is not critical, in principle. However, the N-formyl compound must not contain any active hydrogens, i.e. it should be free from hydroxy groups, carboxy groups and sulfonic acid groups. An especially favorable result is obtained if the free secondary amine, from which the N-formyl compound is derived, has a certain basic nature, in particular PK-values of more than 6, preferable more than 7.

There may be used e.g. N-formyl compounds of a secondary aliphatic or heterocyclic amine having the general formula

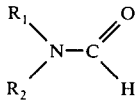

wherein $R_1$ and $R_2$ may be identical or different and represent a straight-chain or branched alkyl radical having 1–3 carbon atoms or a cycloalkyl radical (having 3–8 carbon atoms). Preferred are alkyl radicals having 1–4 carbon atoms and cycloalkyl radicals having 5 and 6 carbon atoms. However, $R_1$ and $R_2$ may also form together a bivalent radical, preferably a bivalent saturated radical. In that latter case, the bivalent radical - together with N of the N-formyl group - forms a heterocycle with 5 to 7 members. The bivalent radical may, for example, represent an alkylene group having 4–6 carbon atoms, e.g. a radical $$-CH_2-CH_2-CH(CH_3)-CH_2-CH_2-$$

or a polymethylene radical having 3 to 6 carbon atoms, e.g. a radical $(CH_2)_4$ or $(CH_2)_6-$. The alkylene group may also be interrupted by hetero groups (preferably 1 hetero group). To such hetero groups belong e.g. oxygen $=N-(C_1-C_4)$-alkyl or $=N-CHO$. There may be used for example the N-formyl compounds of the heterocycles pyrrolidine, piperidine, hexamethylenimine, morpholine, piperazine, N-methyl-piperazine, N-methyl-imidazolidine and oxazolidine. Obviously, the use of a compound with 2 N-formyl groups in the molecule (example: N,N'-diformyl-piperazine) requires only half of the stoichiometric quantity which is necessary, if N-formyl compounds with one N-formyl group in the molecule are used.

When N-formyl compounds with low molecular weight (example: DMF = dimethyl formamide) or with a relatively high molecular weight (example: tristridecyl-amine) are used, tertiary fluorine-containing amines are formed as by-products, the boiling points of which are distinctly different from those of the compounds II and III. This fact facilitates separation by distillation of the reaction mixture.

The process according to the invention may be carried out in such a way — for example — that DMF, solvent and HMPT are charged beforehand and that HFPO as such or usefully diluted with HFP is introduced at about −25° C. Subsequently stirring is continued for several hours at −20° C. to −15° C. Nonreacted HFPO and HFP are evacuated by heating to about −5° C. and condensed in cooling traps. The two phases of the reaction batch are separated and the phase containing the reaction products — most often the lower phase — is distilled. It is easy then to separate the products II and III by fractional distillation.

A surprising advantage of the process as claimed herewith — as compared with the process for preparing compound (II) made known by German Offenlegungsschrift No. 24 34.992 — resides in the fact that the process of the invention results in much better yields and at the same time drastically reduces the quantity of solvent needed (ref. Example 6).

The following Examples illustrate the invention.

EXAMPLE 1

In a three-necked flask, equipped with an agitator, thermometer, intensive cooling device and gas inlet pipe and charged with a mixture of 330 g of DMF (4.25 moles), 60 g of HMPT (0.33 mole) and 50 ml of diethylene glycol dimethyl ether are introduced 3800 g of a mixture of 60–65 weight % of HFPO and 40–35 weight % of HFP at the rate of 20 l/h and at a temperature of 31+° C., then agitated for 13 hours at a temperature from −20° to −12° C. subsequently, the two phases of the mixture are separated and the lower phase is distilled. In the course of heating and distilling unreacted HFPO escapes and is collected in cooling traps (1400 g of HFP containing 17% of HFPO):

$1^{st}$ fraction: boiling point +30° to +75° C. (= 685 g)
$2^{nd}$ fraction: boiling point 115° to 118° C. (= 1484 g) mainly consisting of perfluoro-α-(3,6-dimethyl-1,4-dioxanyl-2-oxy-propionic acid fluoride) corresponding to a yield of 73% calculated on reacted epoxide.

The distillation residue is 65 g.

EXAMPLE 1a

The first fraction of Example 1 (685 g) is washed twice with 200 ml each of acetonitrile, releasing 250 g of α,α-difluorotrimethylamine into the acetonitrile phase which is separated from the heavier phase split off. This latter is distilled and yields 113 g  CF₃—CF₂—CF₂—O—CF(CF₃)—C(=O)—F
boiling point 52°– 56° C

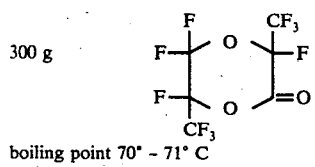
300 g
boiling point 70°– 71° C

EXAMPLE 2

To a solution of 30 g of trisdimethylamino difluorophosphorane (0.149 mole) in 150 ml of diethylene glycol dimethylether in an apparatus as described in (1) are added at a temperature from −40° C. to −30° C., while stirring constantly, 250 g of perfluoro-2-oxo-3,6-dimethyl-1,4-dioxane (0.807 mole) which had been prepared according to Example (1a), stirring is then continued for another hour. At the above stated temperature there are incorporated by condensation 250 g of a mixture of HFPO-HFP (weight ratio 65:35) at a velocity of flow of 20 l/h and vigourous agitation is continued for 5 hours. HFP and excess quantities of epoxide are evacuated by heating to 0° C. and the thus obtained biphasic mixture is separated in a separating funnel. The lower phase is distilled. As a result are obtained 285 g of perfluoro-α-(3,6-dimethyl-1,4-dioxanyl-2-oxy)-propionic acid fluoride (II) having a boiling point of 115°–118° C. (74.3% of the theoretical yield). No more starting material is present.

EXAMPLE 3

780 g of pure HFPO are introduced in analogy to Example (1) at −30° C. and at a velocity of flow of 25 l/h to a mixture of 110 g of dimethyl formamide (1.507mole) and 20 g of hexamethyl phosphoric acid triamide (0.11 mole). This reaction step is followed by 5 hours of agitation at −20° C. and then heating to −5° C. The separated lower phase is washed twice with 200 ml of acetonitrile and distilled:

Boiling point 25°– 115° C = 183 g
boiling point 115°– 118° C = 335 g ⟶
Residue = 26 g

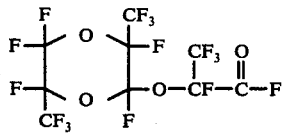

The cooling trap set up after the reaction apparatus and the distillation device contains 120 g of non-reacted epoxide.

EXAMPLE 4

To a mixture of 219 g of DMF (3 moles) and 40 g of HMPT (0.22 mole), charged in an apparatus according to the description of Example (1) are introduced at −15° to −30° C. and at a velocity of flow of 25 l/h 750 g of HFPO (4.25 moles), then stirred at −15° C. for 2 hours. After heating to −5° C. the lower phase is washed twice with 150 ml of acetonitrile and distilled.

As a result are obtained:
boiling point 26°–70° C. = 94 g
boiling point 70°–72° C. = 260 g
boiling point 113°–117° C. = 284 g The fraction which is boiling at a temperature from 70° to 72° C. is perfluoro-2-oxo-3,6-dimethyl-1,4-dioxane; the fraction boiling at 113°–117° C. is perfluoro-α-(3,6-dimethyl-1,4-dioxanyl-2-oxy)-propionic acid fluoride.

EXAMPLE 5

290 g of a mixed product obtained by the reaction of DMF with HFPO according to Example (1), are blended with 50 g of trisdimethylamino difluorophosphorane and 150 ml of tetraethylene glycol dimethyl ether and stirred at −20° C. for 1 hour. Subsequently there are introduced at −30° C. 500 g of hexafluoropropene epoxide (20 l/h) and stirring continued at −20° C. for two more hours.

The two phases formed are separated at 0° C. and the lower phase is washed with 200 ml of acetonitrile and distilled. After first runnings of 73 g there are obtained 526 g of perfluoro-α-(3,6-dimethyl-1,4-dioxanyl-2-oxy)-propionic acid fluoride and a residue of 60 g.

EXAMPLE 6

520 g of DMF, 100 g of HMPT and 100 ml of diethylene glycol dimethyl ether are charged into a 10 liter-stirring apparatus which is equipped with a cooling mantle and otherwise designed according to the description given for Example (1), and 4100 g of an 80%-HFPO are then introduced at −20° to −25° C. Agitation is continued for another 24 hours, the phase which precipitates is separated, washed with acetonitrile and distilled. There are obtained:
1ˢᵗ fraction boiling at 38°–72° C. = 200 g
2ⁿᵈ fraction boiling at 115°–118° C. = 2742 g = 86.2%
calculated on the originally used quantity of epoxide.
Residue = 189 g

EXAMPLE 7

In an apparatus as described in Example 1 are blended at −30° C. 48.5 g (0.5 mole) of N-formyl pyrrolidine in 60 ml of diethylene glycol dimethyl ether with 200 g 60% HFPO which contains 40 weight % of HFP, followed by 30 minutes of agitation. Non-reacted epoxide is evacuated by heating to room temperature. After cooling to −30° C. there are added 40 g of trisdimethylamino difluorophosphorane and further introduced 200 g of 60% HFPO at a metering-in speed of 20 l/h. After 3 hours of additional agitation the precipitating heavier phase is separated at 0° C. and distilled. There are obtained:
Boiling point: 70°–82° C. = 55 g essentially

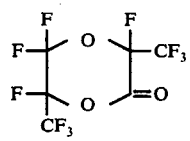

boiling point: 82°–115° C. intermediate fraction (25 g)
boiling point: 115°–118° C. = 45 g

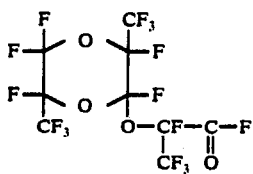

What is claimed is:

1. A process for preparing a mixture of perfluoroalpha-(3,6-di-methyl-1,4-dioxanyl-2-oxy)-propionic acid fluoride (II) and perfluoro-2-oxo-3,6-dimethyl-1,4-dioxane (III) which comprises reacting an N-formylated secondary amine with hexafluoropropene oxide in the presence of 0.01 to 0.5 mols of trisdimethyl amino difluorophosphorane (IV) per mole of amine as a catalyst at a temperature of $-40°$ to $+5°$ C. and using an HFPO/amine ratio of at least 2.5:1 to produce a mixture containing a relatively high proportion of compound (II).

2. A process according to claim 1, which comprises operating at temperatures of from $-25°$ to $-10°$ C.